US009103813B2

(12) United States Patent
Kusinski et al.

(10) Patent No.: US 9,103,813 B2
(45) Date of Patent: Aug. 11, 2015

(54) PROCESSES AND SYSTEMS FOR CHARACTERIZING AND BLENDING REFINERY FEEDSTOCKS

(75) Inventors: Grzegorz Jan Kusinski, Moraga, CA (US); Thomas M. Devine, Moraga, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 513 days.

(21) Appl. No.: 13/331,093

(22) Filed: Dec. 20, 2011

(65) Prior Publication Data

US 2012/0160709 A1 Jun. 28, 2012

Related U.S. Application Data

(60) Provisional application No. 61/427,528, filed on Dec. 28, 2010.

(51) Int. Cl.
*G01N 33/22* (2006.01)
*G01N 33/26* (2006.01)
*G01N 33/28* (2006.01)
*G01N 17/02* (2006.01)

(52) U.S. Cl.
CPC ............ *G01N 33/2823* (2013.01); *G01N 17/02* (2013.01)

(58) Field of Classification Search
CPC ..... G01N 17/02; G01N 21/65; G01N 21/658; G01N 27/026; G01N 27/06; G01N 27/10; G01N 27/14; G01N 33/03; G01N 33/22; G01N 33/28; G01N 33/2805; G01N 33/2823; G01N 33/2876
USPC .................................. 436/6, 60–61, 129, 150
See application file for complete search history.

(56) References Cited

U.S. PATENT DOCUMENTS

| | | | |
|---|---|---|---|
| 3,936,737 A | 2/1976 | Jefferies, Sr. | |
| 4,209,695 A | 6/1980 | Arnold et al. | |
| 4,238,298 A * | 12/1980 | Tsuru et al. | 205/775.5 |
| 4,686,857 A * | 8/1987 | Kato | 73/304 R |
| 4,751,466 A * | 6/1988 | Colvin et al. | 324/449 |
| 4,752,360 A * | 6/1988 | Jasinski | 205/776.5 |
| 4,791,374 A * | 12/1988 | Yodice et al. | 324/439 |
| 4,998,208 A | 3/1991 | Buhrow et al. | |
| 5,015,957 A | 5/1991 | Bessiere et al. | |
| 5,025,222 A * | 6/1991 | Scott et al. | 324/639 |
| 5,045,775 A | 9/1991 | White et al. | |
| 5,068,196 A | 11/1991 | Hays et al. | |
| 5,071,527 A | 12/1991 | Kauffman | |
| 5,146,169 A * | 9/1992 | Morishita et al. | 324/438 |
| 5,155,555 A | 10/1992 | Wetegrove et al. | |
| 5,201,215 A | 4/1993 | Granstaff et al. | |
| 5,274,335 A | 12/1993 | Wang et al. | |
| 5,332,900 A | 7/1994 | Witzke et al. | |
| 5,370,776 A * | 12/1994 | Chen | 205/776.5 |
| 5,411,890 A | 5/1995 | Falat | |
| 5,420,041 A * | 5/1995 | Matsushita et al. | 436/61 |
| 5,425,867 A * | 6/1995 | Dawson et al. | 204/400 |
| 5,475,612 A | 12/1995 | Espinosa et al. | |
| 5,503,006 A | 4/1996 | Babaian-Kibala et al. | |
| 5,546,792 A * | 8/1996 | Becker | 73/64.53 |
| 5,612,490 A * | 3/1997 | Carlson et al. | 73/61.43 |
| 5,638,172 A * | 6/1997 | Alsmeyer et al. | 356/301 |
| 5,712,165 A * | 1/1998 | Alvarez et al. | 436/21 |
| 5,935,863 A * | 8/1999 | Descales et al. | 436/171 |
| 6,028,433 A * | 2/2000 | Cheiky-Zelina et al. | 324/663 |
| 6,053,032 A | 4/2000 | Kraus et al. | |
| 6,229,312 B1 * | 5/2001 | Fleury et al. | 324/376 |
| 6,250,140 B1 | 6/2001 | Kouznetsov et al. | |
| 6,294,387 B1 | 9/2001 | Yepez et al. | |
| 6,469,521 B1 * | 10/2002 | Klun et al. | 324/658 |
| 6,655,221 B1 * | 12/2003 | Aspelund et al. | 73/861.04 |
| 6,683,463 B2 | 1/2004 | Yang et al. | |
| 6,876,193 B2 * | 4/2005 | Schilowitz et al. | 324/698 |
| 7,043,372 B2 * | 5/2006 | Koehler et al. | 702/25 |
| 7,043,402 B2 * | 5/2006 | Phillips et al. | 702/184 |
| 7,109,729 B2 * | 9/2006 | Schilowitz et al. | 324/698 |
| 7,160,728 B2 | 1/2007 | Chimenti et al. | |
| 7,204,128 B1 | 4/2007 | Liu et al. | |
| 7,241,621 B2 * | 7/2007 | Reischman et al. | 436/60 |
| 7,407,809 B2 * | 8/2008 | Reischman et al. | 436/60 |
| 7,456,328 B2 | 11/2008 | Bary | |
| 7,581,434 B1 * | 9/2009 | Discenzo et al. | 73/53.01 |
| 7,589,539 B2 | 9/2009 | Butler et al. | |
| 7,618,822 B2 | 11/2009 | Nemana et al. | |
| 7,698,929 B2 | 4/2010 | Wollenberg et al. | |
| 7,711,486 B2 | 5/2010 | Thigpen et al. | |
| 7,723,115 B2 | 5/2010 | Qian et al. | |

(Continued)

OTHER PUBLICATIONS

Kelly, J. J. et al, Analytical Chemistry 1990, 62, 1444-1451.*
Lvovich, V. F. et al, Electrochimica Acta 2006, 51, 1487-1496.*
Ulrich, C. et al, Sensor & Actuators B 2007, 127, 613-618.*
Morris, R. E. et al, Energy & Fuels 2009, 23, 1610-1618.*
de Lira, L. F. B. et al, Microchemical Journal 2010, 96, 126-131.*

(Continued)

*Primary Examiner* — Arlen Soderquist
(74) *Attorney, Agent, or Firm* — Melissa Patangia

(57) ABSTRACT

Refinery feedstocks can be characterized based on any of: dissociation of acids in the crude, breakup of naphthenic acid molecular associations, and/or dissociation of sulfur compounds in the feedstocks. The characterization is performed as a function of temperature via any of electrical resistivity measurement, vibrational spectroscopic analysis, voltammetry, electrochemical impedance spectroscopy (EIS) and combinations thereof. The method can be practiced in any of refinery, terminal, and laboratories. It can be used in conjunction with models and hardware to optimize the usage of refinery feedstocks in the blending and valuation of the feedstocks. In one embodiment, the characterization of refinery feedstocks is via the use of EIS.

20 Claims, No Drawings

(56) References Cited

U.S. PATENT DOCUMENTS

| | | | |
|---|---|---|---|
| 7,818,156 B2 | 10/2010 | Vachhani et al. | |
| 7,835,875 B2* | 11/2010 | Halalay et al. | 702/50 |
| 7,984,643 B2 | 7/2011 | Butler et al. | |
| 7,985,592 B2 | 7/2011 | Wollenberg | |
| 7,990,161 B2* | 8/2011 | Ju et al. | 324/698 |
| 8,016,998 B2 | 9/2011 | Compton et al. | |
| 8,033,164 B2 | 10/2011 | Dermody et al. | |
| 8,222,605 B2* | 7/2012 | Da Silva et al. | 250/339.08 |
| 8,591,814 B2* | 11/2013 | Hodges | 422/68.1 |
| 2002/0006667 A1 | 1/2002 | Chimenti et al. | |
| 2003/0188995 A1 | 10/2003 | Varadaraj | |
| 2003/0194811 A1* | 10/2003 | Reischman et al. | 436/60 |
| 2003/0222656 A1* | 12/2003 | Phillips et al. | 324/605 |
| 2004/0085080 A1* | 5/2004 | Schilowitz et al. | 324/698 |
| 2004/0106204 A1 | 6/2004 | Chimenti et al. | |
| 2005/0035755 A1* | 2/2005 | Schilowitz et al. | 324/158.1 |
| 2005/0088646 A1* | 4/2005 | Kong et al. | 356/70 |
| 2005/0110503 A1* | 5/2005 | Koehler et al. | 324/710 |
| 2006/0037414 A1 | 2/2006 | C. Blum et al. | |
| 2006/0105467 A1* | 5/2006 | Niksa et al. | 436/150 |
| 2007/0024287 A1* | 2/2007 | Graves et al. | 324/453 |
| 2007/0029196 A1* | 2/2007 | Ishihara et al. | 204/416 |
| 2007/0037288 A1 | 2/2007 | Qian et al. | |
| 2007/0074563 A1* | 4/2007 | Liu et al. | 73/54.24 |
| 2007/0175278 A1 | 8/2007 | Puppels et al. | |
| 2007/0231912 A1* | 10/2007 | Reischman et al. | 436/60 |
| 2007/0295648 A1 | 12/2007 | Falkiner et al. | |
| 2007/0298505 A1 | 12/2007 | Smith et al. | |
| 2008/0022757 A1* | 1/2008 | Zhou et al. | 73/53.05 |
| 2008/0041762 A1 | 2/2008 | Brons et al. | |
| 2008/0102529 A1 | 5/2008 | Butler et al. | |
| 2008/0147365 A1 | 6/2008 | Prasad et al. | |
| 2008/0164137 A1 | 7/2008 | Messer et al. | |
| 2008/0174323 A1* | 7/2008 | Raju et al. | 324/700 |
| 2008/0248967 A1 | 10/2008 | Butler et al. | |
| 2008/0253426 A1* | 10/2008 | Voelkening et al. | 374/27 |
| 2008/0257782 A1 | 10/2008 | Vachhani et al. | |
| 2008/0260584 A1* | 10/2008 | Gudde et al. | 422/69 |
| 2009/0011517 A1* | 1/2009 | Hodges | 436/139 |
| 2009/0114387 A1 | 5/2009 | Horvath Szabo et al. | |
| 2009/0236263 A1 | 9/2009 | Babic-Samardzija et al. | |
| 2009/0294672 A1* | 12/2009 | da Silva et al. | 250/339.08 |
| 2010/0052702 A1* | 3/2010 | Ju et al. | 324/698 |
| 2010/0078358 A1 | 4/2010 | Tullos et al. | |
| 2010/0100404 A1 | 4/2010 | Hodges et al. | |
| 2010/0155262 A1* | 6/2010 | Yepez et al. | 205/775.5 |
| 2010/0185401 A1 | 7/2010 | Hernandez et al. | |
| 2010/0193377 A1 | 8/2010 | Wang et al. | |
| 2010/0211329 A1* | 8/2010 | Farquharson et al. | 702/28 |
| 2010/0252727 A1* | 10/2010 | Seastrom | 250/282 |
| 2010/0299105 A1 | 11/2010 | Vass et al. | |
| 2011/0223672 A1* | 9/2011 | Tumiatti et al. | 436/6 |
| 2011/0308790 A1 | 12/2011 | Strapoc et al. | |
| 2012/0022694 A1* | 1/2012 | Mohanty et al. | 700/271 |
| 2012/0160707 A1* | 6/2012 | Kusinski et al. | 205/775 |
| 2012/0160709 A1* | 6/2012 | Kusinski et al. | 205/782 |
| 2012/0166099 A1* | 6/2012 | Kusinski et al. | 702/25 |

OTHER PUBLICATIONS

U.S. Appl. No. 13/331,130, filed Dec. 20, 2011, Kusinski et al.
U.S. Appl. No. 13/331,114, filed Dec. 20, 2011, Kusinski et al.
U.S. Appl. No. 13/331,155, filed Dec. 20, 2011, Kusinski et al.
Messer et al., New Theory for Naphthenic Acid Corrosivity of Athabasca Oils ands Crudes, 2004, Corrosion.
R. Kalvoda, Adsorptive Stripping Voltammetry in Trace Analysis, Pure and Applied Chemistry, 1989, vol. 61, No. 1, pp. 97-112.
Kalvoda R., Rewiew of Adsorptive Stripping Voltammetry—Assessment and Prospects, (1994), Fresenius J. Anal. Chem. 349; 565.
Ok-Sun Kim et al., Cyclic Voltammetry of Lipophilic Compounds in Oil: Direct Determination of Lipid Peroxide with a Carbon Past Electrode (1995) JAOCS, vol. 72, No. 3 pp. 299-303.
Stanton Ching et al., Cyclic Voltammetry with Ultramicroelectrodes 1994, Chem. Educ., 71 (7), p. 602.
Yepez, Influence of different sulfur compounds on corrosion due to naphthenic acid, (2005), Fuel 84 97-104.
Yepez, On the chemical reaction between carboxylic acids and iron, including the special case of naphthenic acid (May 2007), Fuel, 86 (7-8), p. 1162-1168.
Zeinalov et al., Petroleum acids and Corrosion, Petroleum Chemistry, 2009, vol. 49, No. 3, pp. 185-192.
Qu et al, High Temperate Naphthenic Corrosion of Typical Steels Feb. 2011, Canadian Journal on Mechanical Sciences and Engineering vol. 2, No. 2.

* cited by examiner

US 9,103,813 B2

PROCESSES AND SYSTEMS FOR CHARACTERIZING AND BLENDING REFINERY FEEDSTOCKS

CROSS-REFERENCE TO RELATED APPLICATIONS

This application claims benefit under 35 USC 119 of U.S. Provisional Patent Application Nos. 61/427,540 with a filing date of Dec. 28, 2010.

TECHNICAL FIELD

The invention relates generally to systems and methods for characterizing crude oils and refinery feedstocks according to their corrosivity. In one embodiment, the invention relates to systems and methods for blending crude oils and refinery feedstocks to produce a final feedstock of desired characteristics.

BACKGROUND

Numerous systems and methods have been disclosed to characterize and treat crude oils or refinery feedstocks that contain acids in several forms. The acids in the feedstocks may be organic acids such as carboxylic or naphthenic or mineral acids such as hydrochloric, phosphoric, hydrogen sulfide and various oxidized forms of hydrogen sulfide such as sulfuric acid. Naphthenic acid is a type of organic acid commonly present in acidic crudes. There are publications teaching the treatment and prevention of acid corrosion in petroleum feedstocks with the demineralization and alkali treatment of crude oil, the use of organic corrosion inhibitors, and selection of equipment and materials for handling petroleum feedstocks by alloying metals with anticorrosive additives, such as Cr, Mo, Ni, etc.

Evaluation of corrosivity of refinery feedstocks has typically been done by a classic model considering the Total Acid Number (TAN) of the feedstocks. The TAN number is computed based on milligrams of KOH required to neutralize one gram sample of the crude. If the feedstock has a TAN greater than 0.5, the crude is usually considered corrosive. One traditional approach has been blending high naphthenic acid crudes with low naphthenic acid crudes to a predetermined TAN number, e.g., below 0.5 for crudes or 1.5 for certain side-cuts, such as vacuum gas oil, or by avoiding refining crudes having relatively high quantities of naphthenic acids. US Patent Application No. 2008/0164137 discloses that naphthenic acid corrosivity can be correlated with the chemical composition of naphthenic acids, especially with respect to the ratio between an alpha fraction and a beta fraction of the naphthenic acids There is still a need for improved methods and systems to characterize refinery feedstocks by their corrosivity characteristics.

SUMMARY OF THE INVENTION

In one aspect, a method for evaluating the corrosivity of a crude oil is disclosed. The method comprises: withdrawing a representative sample of a crude oil feedstock; performing impedance measurements on the crude oil as a function of temperature to obtain a first electrochemical impedance (EI) spectrum; obtaining a second EI spectrum on a reference crude oil having known corrosion properties, wherein the first and second EI spectra include data for at least three frequencies; and analyzing the first EI data relative to the second EI data to evaluate the corrosivity of the crude oil feedstock, wherein comparing the first EI data with the second EI data includes comparing at least one of a resistance measurement and a capacitance measurement. In one embodiment, EIS is conducted using a two-electrode cell in which one electrode is an ultramicroelectrode and the second electrode is a reference electrode. In one embodiment, both electrodes are composed of platinum.

In one aspect, a linear voltammetric method to characterize refinery feedstocks is disclosed, wherein current passing through the feedstock is measured as a function of the applied DC voltage. As increasing/decreasing voltage is applied at a constant rate with time, oxidation/reduction of corrosive species such as acids occurs, allowing the use of voltammetry to characterize the feedstock with respect to is its corrosion property. In one embodiment, ultramicroelectrodes made of an electrochemically stable conductor such as platinum are used for the procedure.

In another aspect, a method to characterize and/or optimize blends of refinery feedstocks is disclosed with the use of cyclic voltammetry, wherein blends of feedstocks with measured values are characterized, optimized and compared with a pre-determined value of a crude oil with a known corrosion rate, creating an optimized blend. In one embodiment, electrochemically stable ultramicroelectrodes are employed for the cyclic voltammetric evaluation of refinery feedstocks.

In one embodiment, a two-electrode electrochemical is employed for characterizing the solutions by either linear voltammetry and/or cyclic voltammetry, with the ultramicroelectrode serving as the working electrode and a second electrode having a higher surface area serving as both the reference electrode and the counter electrode.

In one aspect, a method is disclosed for evaluating the corrosivity of a crude oil feedstock by correlating its corrosivity with dissociation of acids in the crude oil. The method comprises: withdrawing a representative sample of the crude oil feedstock, wherein the crude oil sample has a certain amount of acids; detecting the dissociation of the acids in the crude oil feedstock as a function of temperature by obtaining any of impedance measurements, linear voltammograms and cyclic voltammograms over a range of temperature from ambient to 700° F.; providing respective impedance measurements, or linear voltammograms, or cyclic voltammograms of a reference oil feedstock having a known dissociation of acids; and comparing the measurements of the crude oil feedstock with the measurements of the reference oil feedstock to evaluate the corrosivity of the crude oil feedstock.

In yet another aspect, a method is disclosed for evaluating the corrosivity of a crude oil feedstock by correlating its corrosivity with the electrical resistivity of the crude oil. The method comprises: withdrawing a representative sample of the crude oil feedstock, wherein the crude oil sample has a certain amount of corrosive species; detecting the corrosive species in the crude oil feedstock as a function of temperature by obtaining the electrical resistivity over a range of temperature from ambient to 700° F.; providing electrical resistivity measurements of a reference oil feedstock having a known dissociation of acids; and comparing the electrical resistivity measurements of the crude oil feedstock with the electrical resistivity measurements of the reference oil feedstock to evaluate the corrosivity of the crude oil feedstock. In one embodiment, the four-point probe is employed for the resistivity measurement. The four-point probe is housed in a holder that is relatively chemically inert in the test solutions and which exhibits a high electrical resistance.

In another aspect, a method is disclosed to evaluate the corrosivity of a crude oil feedstock by vibrational spectroscopic analysis as a function of temperature. The method comprises: withdrawing a representative sample of the crude oil feedstock having a certain amount of acids; detecting molecular associations and dissociation of acids in the crude oil feedstock as a function of temperature from ambient to 700° F. by vibrational spectroscopic analysis to obtain spectroscopic measurements; and analyzing the vibrational spectroscopic measurements to correlate the molecular associations and dissociation of the acids in the crude oil feedstock to evaluate its corrosivity as a function of temperature.

In yet another one aspect, a method for optimizing blends of refinery feedstock is disclosed. The method comprises: providing a plurality of refinery feedstock samples with each feedstock sample being representative of a feedstock stream to the refinery; obtaining a vibrational spectroscopic measurement as a function of temperature for each of the feedstock samples; providing a database correlating vibrational spectroscopic measurements with known corrosion performance of reference refinery feedstock; using the spectroscopic measurement of the refinery feedstock samples and the database correlating vibrational spectroscopic measurements with corrosion performance of reference refinery feedstock to obtain an optimized feedstock blend having desired vibrational spectra over a temperature range from ambient to 700° F., correlating with an acceptable corrosion performance.

In another aspect, a method to optimize feedstock blends is disclosed. The method comprises: providing a plurality of refinery feedstock samples with each feedstock sample being representative of a feedstock stream to the refinery; obtaining vibrational spectroscopic measurements as a function of temperature for the feedstock blend and the plurality of refinery feedstock samples; blending the feedstock samples in pre-determined proportions to form a feedstock blend; comparing the vibrational spectroscopic measurements of the feedstock blend to pre-determined vibrational spectroscopic measurements; and adjusting the proportions of the feedstock samples so that the vibrational spectroscopic measurements of the feedstock blend are comparable to the pre-determined vibrational spectroscopic measurements.

In one aspect, a system to optimize blends of crude oil feedstock to a refinery to minimize corrosion impact is disclosed. The system comprises: an on-line analyzer for obtaining any of electrochemical impedance measurements, linear voltammograms, cyclic voltammograms, and two-point probe or four-point probe measurements of electrical resistivity as a function of temperature for plurality of refinery feed streams to the refinery; a database correlating the measurements with at least one of molecular break-up of acid molecules in crude oil feed, dissociation of acids in crude oil feed, and dissociation of sulfur compounds into ionic species in refinery feed; and an operator, operatively disposed to receive the measurements from the on-line analyzer and the database correlating the measurements with corrosion characteristics of crude oil feedstock, and wherein the operator modifies a blend of the refinery feed streams in response to the received information. In one embodiment, the on-line analyzer is for obtaining spectroscopy measurements as a function of temperature.

DETAILED DESCRIPTION

The following terms will be used throughout the specification and will have the following meanings unless otherwise indicated.

As used herein, the term "refinery feedstock" refers to natural and synthetic liquid hydrocarbon products including but not limited to crude oil, synthetic crude biodegraded oils, petroleum products, intermediate streams such as residue, naphtha, cracked stock; refined products including gasoline, other fuels, and solvents. The term "petroleum products" refer to natural gas as well as crude oil, solid, and semi-solid hydrocarbon products including but not limited to tar sand, bitumen, etc.

Crudes and crude blends are used interchangeably and each is intended to include both a single crude and blends of crudes.

References to naphthenic acid ("NA") include naphthenate and vice versa unless the context clearly specifies otherwise. The term naphthenic acid refers to all of the carboxylic acid content of a crude oil including but not limited to alkyl substituted acyclics (including "fatty" acids), aromatic acids, carbazoles, and isoprenoid acids. Examples in certain crude oils include complex acid structures with two, three, and even four carboxylic groups (tetrameric acids as well as structures containing heteroatoms (O, $O_4$, S, OS, $O_2S$, $O_3S$, N, NO, $NO_2$, $N_2O$).

In one embodiment, the invention relates to methods and systems for characterizing the corrosivity of refinery feedstocks, e.g., crude. The corrosivity of a crude can be characterized by and related to any of the following factors and combinations thereof:

1) The association of the acids in the crude into dimers, trimers, etc., where the acid associations are not corrosive. Hence, knowledge of acids tendency to form complex multi molecule associations is important. For different acid types such complex associations are stable, however, they can de-associate at elevated temperature, e.g., the critical temperature of de-association or breakup (TCRBr). Below the TCRBr, the feedstock is not corrosive, and above the TCRBr the feedstock is corrosive. For different crudes and feedstocks with different organic acids the tendency to associate will be different and, hence, the TCRBr will be different.

2) The dissociation of acids (and/or acidic species) in the crude. Acid dissociations are also a strong function of temperature and traces amount of water and other species that have a dielectric constant higher than the crude matrix.

3) The presence of and dissociation of specific sulfur compounds in the crude into corrosive species.

4) The formation of protective surface films on certain equipment materials upon contact with the crude.

5) The influence of key elemental metals on corrosion resistance of equipment materials upon exposure to the crude.

Characterizing Corrosion Property Via Dissociation of Acids in the Crude:

Crude most likely originates from organic debris associated with plants and animals, thus explaining the vast number of chemical species found in crudes and the considerable variability in chemical composition of crudes from different parts of the world. Generally, the hydrocarbons in crude can be subdivided into four large classes: alkanes, cycloalkanes, aromatics, and cycloalkanoaromatics.

Alkanes are often termed paraffins and are separated into two groups: normal alkanes and isoalkanes. Cycloalkanes are also called naphthenes and are ring compounds and are completely saturated with hydrogen and sometimes contain alkyl side chains. Aromatics typically contain between one and four benzene rings and are characterized by high boiling points. Examples of aromatics are benzene, which is found in gasoline, and 2-methylbiphenyl, which is present in diesel fuel. Cycloalkanoaromatics consist of fused aromatic and cycloalkane rings, often with alkyl branches on the rings. 1-Methylindane is a cycloalkanoaromatic found in kerosene.

The values of the dielectric constant of the hydrocarbon classes indicated above are all around 2, much lower than the dielectric constant of water of about 80 at room temperature. For example, hexane (an alkane) has a dielectric constant of 2.02, cyclopentane and cyclohexane (cycloalkanes) have values of 1.97 and 2.02 respectively; benzene (an aromatic) has a value of 2.28. The low value of the dielectric constant suggests that the carboxylic acids dissolved in oil/crude will be undissociated, indicating that free protons ($H^+$) per se are not the cause of corrosion of steels in crudes that contain naphthenic acid ("NA").

It is believed that the above hydrocarbons are not reactive toward carbon steel but they serve as solvents for corrosive species such as naphthenic acid and certain sulfur compounds. The degree of dissociation of acids in the crude can be indicative of the crude's corrosivity by electrochemical mechanisms, as opposed to chemical mechanisms. In the case of NA, the electrochemical mechanism of corrosion is caused by dissociation of the naphthenic acid: $R(CH)_{2n}COOH \rightarrow R(CH)_{2n}COO^- + H$. The electrochemical mechanism of corrosion of steel comprises of the combination of the electrochemical reduction of $H^+$ to $H$, and the electrochemical oxidation of $Fe$ to $Fe^{+2}$.

Measuring Corrosion Property Via Breakup of NA Molecular Associations:

In one embodiment of a system to evaluate the corrosivity of a crude, the degree of break-up of NA molecular associations such as dimers, trimers, tetramers, micelles, as well as unassociated molecules is measured. It is known that significant hydrogen bonding exists between carboxylic acid molecules because of the polar character of their COOH group. The hydrogen bonding results in the formation of molecular dimers, in which two carboxylic acid molecules are strongly associated with each other. Associated molecules, such as dimers and trimers, are believed to be less corrosive to metals than unassociated carboxylic acid molecules.

It is believed that the temperature dependence of corrosion is dependent, at least in part, on the decomposition of dimers and trimers into unassociated, individual molecules that are more corrosive to metals. Given that the structures of many carboxylic acids that make up NAs contain a polar end group (e.g., —COOH) and a nonpolar end (e.g., linear alkanes and aromatic rings), in one embodiment the carboxylic acids is believed to form larger molecular associations than dimers and trimers, i.e., micelles which lowers the crude's corrosivity by removing larger numbers of individual carboxylic acid molecules from solution. Therefore, in one embodiment of a system to characterize the corrosivity of crudes, the break-up of molecular associations in the crude is measured to correlate with its corrosivity. In another embodiment, the formation and stability of molecular associations of NAs is measured as a function of temperature.

Various types of dimers are possible, but the cyclic structure is believed to be the most stable one. It is also believed that water molecules can weaken the stabilization energy of the molecular associations of acids. Proportion of free acids is a function of dimerization free energy: $K_d = n_{Dimer}/n_{monomer}^2 = \exp(-\Delta G/RT)$, and the higher the $K_d$ the higher is the fraction of dimers. Binding energies are stronger (higher $K_d$) in low dielectric constant environments. A typical stable cyclic dimer structure is one in which two carboxyl groups form two hydrogen bonds with each other (Dimer 1—D1). A water molecule can change dimer configuration by inserting itself between two carboxylic groups in several ways: 1) from the second acid monomer, O atom in carbonyl group doesn't participate in the H-bonding. Instead, H-bonding comes from H and O in the same OH group (Dimer 2—D2). 2) OH group in the second acid monomer is free of hydrogen bonding. Instead, one H atom from radical chain (attached to C2) participates in the hydrogen bonding (Dimer 3—D3). It is believed that the dimerization energies of cyclic dimers D1 are always higher than those of D2 and D3 for all naphthenic acids, hence, it is believed that water will lower the critical temperature for de-dimerization.

Characterizing Corrosion Property Via Dissociation of Sulfur Compounds:

It is known that there are a number of different sulfur compounds present in crude, including aliphatic sulfides, disulfides, mercaptans, polysulfides, and thiophenes. In a refinery, sulfur compounds in the crude cause corrosion via different means: direct reaction with steel equipment producing corrosion products such as iron sulfide, reaction of the sulfur compounds generating corrosive $H_2S$, and the thermal decomposition of some sulfur compounds above 500° F. which produces $H_2S$. It is believed that the dissociation of sulfur compounds into ionic species is a factor contributing to the corrosivity of a crude. Additionally, it is believed that sulfur compounds in a crude facilitates or makes possible the dissociation of the acids in the crude.

Characterizing Corrosion Property Via Quartz Crystal Microbalance:

In one embodiment, quartz crystal microbalance (QCM) is employed to simultaneously measure the mass changes of samples in the crude as well as the changes in the properties of the crude as a function of temperature. The samples comprise carbon steel or other structural materials commonly used for corrosion studies. The QCM is configured with electrodes on both sides of a thin disk of quartz, and a sample (e.g., carbon steel) is interposed between the QCM and the crude. The sample can be applied onto the QCM by electroplating.

At least one resonant frequency of the QCM is measured simultaneously with the admittance magnitude at the resonant frequencies. The resonant frequency is correlated with the admittance magnitude. The admittance/frequency correlation is then applied to an equivalent circuit model. The sample's solid mass loss in a particular crude can be derived from the correlated admittance/frequency data.

Methods for Characterizing Refinery Feedstocks:

Depending on the crude sample, some preparation may be needed. Preparation for sample analysis prior to characterization may include appropriate steps to remove particulate and/or solid matter, excess water, or other impurities. Excess water may be removed by a process of alternate heating and cooling of the sample, followed by centrifugation to remove the water. Alternatively, the water may be removed manually. The heating process may be carried out in an inert atmosphere, e.g. under vacuum, nitrogen or helium or other inert gases.

In one embodiment, the characterization is carried out with crude oils being maintained over a range of temperatures representative of the operation in a refinery, e.g., from ambient to 750° F., from 100° F. to 400° F., from 0° F. to 400° F., etc. In one embodiment, the measurements are carried out as a function of temperature (200° F.-750° F.) to show the dissociation of sulfur compounds in the crude into anions and cations, contributing to the electrochemical mechanism of corrosion. In one embodiment, a vacuum is pulled on a sample to achieve a higher boiling point at a given temperature, simulating vacuum distillation conditions. Under vacuum distillation, the relative volatility of components increase, thus reducing the temperature required to bring acids and hydrocarbons to their boiling point, avoiding degradation. Vacuum distillation increases the relative volatility of the key components in many applications. The higher the relative volatility, the more separable are the two components; this connotes fewer stages in a distillation column in order to effect the same separation between the overhead and bottoms products. Lower pressures increase relative volatilities in most systems. A second advantage of vacuum distillation is the reduced temperature requirement at lower pressures. For many systems, the products degrade or polymerize at elevated temperatures, hence, by reducing the pressure and hence, reducing the temperature, certain degradation effects can be avoided.

In one embodiment, the evaluation is carried out with crude oil feeds having different oxygen concentrations, e.g., from oxygen free oil (crude oil with low $O_2$ of less than 10 ppm) to oxygen having a much higher concentration of oxygen. In one embodiment, crude oil feeds enriched with an oxygen concentration ranging from 10 ppm to 500 ppm are tested. In another embodiment, the evaluation is carried out with crude oil feeds having different water and/or steam concentration to simulate the conditions existing in operations such as desalting, steam stripping. In one embodiment, the level ranges from 10 ppm to 2%.

In one embodiment, the molecular associations in crude can be evaluated using characterization techniques including but not limited to vibrational spectroscopic analysis, and voltammetry and other electrochemical techniques known in the art. The characterization can consist of any of linear and cyclic voltammetry, electrochemical impedance spectroscopy (EIS), anodic and cathodic polarization, two-point probe and four-point probe resistivity measurements, quartz crystal and gallium phosphate crystal microbalance measurements of corrosion rate, and vibrational spectroscopic analysis. In one embodiment, ultramicroelectrodes can be used with any of linear and cyclic voltammetry, electrochemical impedance spectroscopy, and anodic and cathodic polarization in the measurement of refinery feedstocks, blends, and simulations of crudes. In another embodiment, resistance probes are used for detecting/monitoring corrosion of coupons and equipment during processing of corrosive crudes.

In one embodiment, voltammetric signals of reference crude oil samples at various temperature(s), oxygen level(s), steam/water level(s), and/or other variables, are measured before and after adding known concentrations of acids. As increasing/decreasing voltage is applied at a constant rate with time, oxidation/reduction of corrosive species such as acids occurs, allowing the use of voltammetry to characterize the feedstock with respect to is its corrosion property. Voltammetric signals of various crude oil feeds to a refinery are measured and compared to the signals of the reference crude oil feedstock having known acid dissociation activities, and hence known corrosion rates. The measured signals can be used to optimize a blend of the oil feedstock. Results based on current, voltage, and time relations are measured, as oxidation/reduction of corrosive species occurs with the applied voltage. The system can be an on-line or off-line system, wherein current passes through samples of refinery feedstock as a function of the potential applied.

In one embodiment to characterize the solutions (e.g., refinery feedstock, crudes, and laboratory simulations of refinery feedstock and crude) by linear voltammetry and cyclic voltammetry, a two-electrode electrochemical cell is employed. The measured current being indicative of the electrochemical reduction of potentially corrosive species. In the two-electrode cell, the first electrode is an ultramicroelectrode (UME) that serves as the working electrode (WE) In one embodiment, the working electrodes are as small as practically possible, and depending on the conductivity of the medium, it can be 100 µm, 10 µm, or even 1 µm or less. In one embodiment, ultramicroelectrodes made of an electrochemically stable conductor (e.g., platinum) are used to reduce the electrochemical cell's IR-drop, which in cells containing crude would otherwise be so large as to preclude control of the electrode's electrochemical potential. The second electrode has a much higher surface area, and serves as both the reference electrode (RE) and counter electrode (CE) of the two-electrode cell. The second electrode in one embodiment is made of a metal such as platinum, which forms a non-polarizable interface with crude. The ultramicroelectrode can be made of various metals or alloys or conductive materials. In one embodiment, platinum or gold is employed, exhibiting a low hydrogen overvoltage. As used herein, ultramicroelectrodes refer to electrodes having dimensions on the order of micrometers or less, e.g., Pt electrodes with diameters of 1, 10, 25, and 50 µm.

In another embodiment, cyclic voltammetry is employed, wherein blends of feedstocks with measured values are optimized and compared with a pre-determined value of a crude oil that causes a known corrosion rate of carbon steel, creating an optimized blend. In one embodiment, the dissociation of corrosive species is assessed by measuring the point at which the cathode effect commences. The "cathode effect" is the effect wherein as the voltage across the cell is algebraically lowered beyond a certain point the current of the cell rises. The electrochemical reduction of protons in the crude oil can be calculated by the potential at which the cathode effect occurs. For example, the potential at the cathode effect may be found for each sweep by determining the point at which the current first drops to ½ of its maximum value. The changes in the currents during the DC potential sweep are recorded to provide a plot of DC currents vs. DC potential. The plots provide characteristic of current spectra or "fingerprints" for the electrochemical reduction of acids present therein.

In one embodiment, electrochemically stable ultramicroelectrodes are employed for the cyclic voltammetric evaluation of refinery feedstocks. The ultramicroelectrode is made of an electrochemically inert material (e.g., platinum). The second electrode has a large surface area and is a combination reference/counter electrode which is also made of platinum. Automatic cycle generation occurs at a constant rate (e.g., rising at between 1 and 50 volts per second), then falling at an identical rate, with means for deriving readings from a statistically significant number of cycles (e.g., between 2 to 20 cycles).

In one embodiment, the characterization is via spectroscopic analysis, using any of impedance spectroscopy, ultraviolet absorption spectroscopy, visible absorption spectroscopy, infrared absorption spectroscopy, ultraviolet scattering spectroscopy, visible scattering spectroscopy, infrared scattering spectroscopy, fluorescence spectroscopy, Raman spectroscopy, and Nuclear Magnetic Resonance (NMR). In one embodiment, the corrosion property of a crude is measured via Raman spectroscopy, wherein the Raman spectrum is obtained by passing a laser beam (e.g., 750 nm wavelength) through a thin film of crude contained in a quartz cuvette. The long wavelength of the laser minimizes fluorescence, which would swamp the relatively weak Raman scattered radiation. In one embodiment, the Raman scattered light exiting the cell is collected, collimated, notch-filtered, and focused into a spectrometer wherein a recorder is used to record the intensity of the dispersed radiation.

In one embodiment of the crude characterization system, electrochemical impedance as a function of temperature is measured to show the dissociation of the acids in the crude. Values of resistance and dielectric constant are derived to show the corrosivity trend, e.g., crudes with high dielectric constant (and conversely lower electrical resistivity) are more corrosive. The higher the dielectric constant, the more likely that the acids will dissociate thus increasing the likelihood that the crude is corrosive.

The construction and operation of impedance spectrometers are known, and commercial impedance spectrometers are available. IS instrumentation generally comprises an array of impedance and frequency response analyzers, as well as "lock-in" amplifiers. The equipment provides a source of AC signals of varying frequency and constant amplitude. The IS equipment also provides circuitry for detecting the magnitude of electric current conducted through the sample. IS data in one embodiment are measured for at least three frequencies, e.g., including at least one frequency less than one Hertz, and at least one frequency on the order of 100 Hertz in one embodiment, and greater than 10 kilohertz in another embodiment.

As with voltammetric evaluations, EIS can be conducted using a two electrode cell in which one electrode is an ultramicroelectrode and the second electrode is a reference electrode. The reference electrode provides an inert surface on which particular species in the solution, e.g., refinery feedstock, crude, laboratory simulations of refinery feedstock and crude, can come into thermodynamic equilibrium. In some embodiments in which measurements are conducted at temperatures below the decomposition temperature of ferrocene, ferrocene can be added to the test solution in order to establish the ferrocene/ferrocinium equilibrium at the (reference) electrode.

In one embodiment of the method, impedance spectroscopy (IS) data of a crude oil is compared to the IS data of a control sample, i.e., a crude oil having known corrosion characteristics including corrosion rate and performance under different operating conditions and/or upon contact with different materials. In an exemplary procedure, the following steps are performed: withdrawing a representative sample of the crude oil feedstock, wherein the crude oil sample has a certain amount of corrosive species; detecting the corrosive species in the crude oil feedstock as a function of temperature by obtaining the electrical resistivity over a range of temperature from ambient to 700° F.; providing electrical resistivity measurements of a reference oil feedstock having a known corrosivity towards carbon steel; and comparing the electrical resistivity measurements of the crude oil feedstock with the electrical resistivity measurements of the reference oil feedstock to evaluate the corrosivity of the crude oil feedstock.

In one embodiment, a four-point probe is employed to measure the resistivity of the sample. The two-point probe is housed in a holder that is relatively chemically inert in the test solutions and which exhibits an extremely high electrical resistance. In one embodiment, the arrangement consists of two identical platinum disk-shaped electrodes of small diameter (e.g., 10 µm) embedded in a high purity quartz holder. In one embodiment, in order to maximize the holder's electrical resistivity, the quartz is of the highest purity obtainable.

Corrosion analysis using EIS data and/or other readings including derived data such as electrical resistivity, dielectric constant reading, etc., can be performed using known statistical techniques. Examples include Complex Non-Linear Least Squares fitting technique, Principal Component Analysis (PCA), Multivariate Least Squares Regression (MLR), Principal Component Regression (PCR), Pattern Recognition Analysis, Cluster Analysis, and Neural Net Analysis, and the like. In yet another embodiment, corrosion analysis is performed with the use of a look up table, which maps various critical values, e.g., electrical resistivity, dielectric constant values identified for a crude oil feedstock, for example, by earlier experimentation for reference crude oil samples.

For the characterization of reference crude oil samples, direct measurements of the dynamic corrosion rates of carbon steels, stainless steels, and other structural materials that are employed in refineries is obtained to quantify the corrosivity of refinery feedstock, crude, and laboratory test solutions that simulate refinery feedstock and crude. Refinery feedstock and crude with quantitatively determined corrosivities serve as standards for evaluating the capabilities of any of EIS, linear and cyclic voltammetry, four-point probe resistivity, and vibrational spectroscopy to characterize the corrosivities of unknown crude and refinery feedstock. A plurality of samples are employed to build a database correlating the molecular association characteristics of the reference samples with their known corrosion performance (e.g., measured corrosion rates) as a function of temperature.

In one embodiment, direct measurements of the dynamic corrosion rates of a refinery's structural materials can be conducted by crystal microbalance measurements of weight changes in samples of the structural materials immersed in refinery feedstock, crude, and laboratory solutions that simulate refinery feedstock and crude. The dynamic corrosion rate measurements will be conducted over the range of temperatures present inside operating refineries, e.g., from ambient to 700° C., and the measurements will be made as a function of time, for times up to several weeks.

In one embodiment, the samples consist of thin films of structural materials deposited (by selected thin-film deposition techniques) onto quartz crystals and gallium phosphate crystals. Quartz crystals are effective for tests conducted at temperatures of 300° C. or lower. Gallium phosphate crystals are suitable for temperatures higher than the highest temperatures typically found in operating refineries, e.g., over 500° C. If the corrosion attack is uniform across the sample's surface, then the corrosion rate is given by measurements of weight change divided by surface area divided by the time interval during which the weight loss occurred. Since the sample's weight is monitored continuously with time, the corrosion rate is determined continuously with time. If the corrosion attack is nonuniform across the sample's surface, the sample's weight change will be continuously measured.

In the reference database, corrosion data for the referenced refinery feedstock, crude, and laboratory test solutions are correlated to the acid stability characteristics of the samples (both in terms of acid dimerization energies and acid dissociation energies). The reference database can be used to characterize the corrosivity of a refinery feedstock, as well as in the optimization and blending of feedstock. For example, acid stability measurements of a refinery feedstock are correlated to the acid stability data of the reference samples with known corrosion rates to predict or anticipate the corrosion characteristics of the feedstock.

In another example of a reference database, measurements made with crystal microbalances reflecting continuous measurements of weight changes of samples in the refinery feedstock are correlated with known measurements in referenced refinery feedstock, or laboratory-simulated crudes. The correlation based on crystal microbalances measurements can be used by itself, or can be used in conjunction with other correlations, e.g., based on molecular association characteristics of the feedstock or laboratory-simulated crudes.

Applications of the Characterization Method:

The method for characterizing or evaluating/predicting the corrosivity of a crude based on the dissociation/association of acids and/or sulfur compounds in the crude can be particularly useful as a screening tool for oil and refinery fractions, new fields, refinery crude oil slates, and product streams. The method can also be used on current refinery and production operations for troubleshooting problems.

The method can be used by supply personnel, planners, and database managers to evaluate candidate raw materials (feedstocks) to make purchasing and pricing decisions based on the corrosivity characteristics of the feedstocks. When embodied in a transportable analyzer configuration, the method can provide on-the-spot evaluations of raw materials prior to the commitment to purchase large quantities.

Samples of refinery feedstock or crude include crude oil directly, or from sludges, oil deposits, oil emulsions, or tars which have been prepared from sample analysis. The crude may be a raw extract from a ground reservoir of oil following extraction, or it may be present in a refinery product stream, such as a distillate, fraction, or other residue from a process unit. The crude may also be dispersed in water. In one embodiment, the method is applicable to the analysis of waste water from a refinery where the crude is dispersed in the water (aqueous corrosion). Aqueous corrosion is electrochemical whereas corrosion caused by crude might be chemical, electrochemical, or both. In one embodiment, the method is employed to determine how corrosive species might preferentially partition between the aqueous phase and the organic phase.

Optimizing Crude Blending Strategy:

The methods for characterizing the corrosion characteristics of crudes based on parameters such as dissociation of sulfur compounds, break-up of NA molecular associations, dissociations of the acids/acid species, etc., can be used for defining and recommending blend ratios for optimal blends depending on the operating conditions and materials of construction of a particular refinery. There are a number of different parameters that can be used to characterize the corrosivity of a crude or blend depending on the ultimate application, e.g., the refinery operating conditions, treatment plans for the crude, refinery equipment characteristics, etc.

For each crude, the threshold concentrations of corrosive species, such as NA, can be calculated once the mechanism of corrosion is identified along with the values of the fundamental parameters, equilibrium constants $K_{eq}$ and rate constants $k_{ox}$. Once the threshold values of compositional parameters of the crudes are defined, a theoretical-based blending strategy can be defined for an optimal blend of crudes having different corrosion characteristics. Depending on the crude, the critical parameter may not be limited to the concentration of naphthenic acid alone. In one embodiment, the critical parameter is the concentration of a particular sulfur compound. In another embodiment, the critical parameter is a combination of the concentrations of acids and sulfur compounds. In yet another embodiment, the critical parameter(s) can be the dielectric constant and/or the electrical resistivity of the crude oil as a function of temperature. In yet another embodiment, the critical parameter is set up to meet a target value consistent with safe and economical operations of a refinery in the context of corrosion management. In yet another application, the critical parameter can be monitored in the various process feed streams in order to maintain instantaneous and time-averaged parameter values within a desired limit.

In one embodiment, wherein the concentration of NA in the crude is used as a key parameter to characterize a crude, a critical TAN value can be defined as a consequence of thermodynamic considerations or kinetic effects. For example, the formation of soluble iron naphthenate above a critical value of TAN can be expressed by the equilibrium constant of the reaction:

$$Fe + 2R(CH_2)_n COOH \rightarrow (R(CH_2)_n COO)_2 Fe + H_2$$

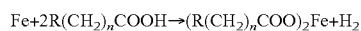

$$K_{eq} = [(R(CH_2)_n COO)_2 Fe][H_2]/[R(CH_2)_n COOH]^2$$

Therefore for a given operating temperature (i.e., given value of $K_{eq}(T)$), a critical value of NA concentration (activity) can be defined, above which iron corrodes to form soluble iron naphthenate.

$$[NA]_{threshold, thermo} = \{[Fe\ Naphthenate][H_2]/K_{eq}\}^{1/2}$$

Thus a blending strategy would be to blend to $[NA] < [NA]_{threshold, thermo}$, because at such concentrations the crude would be non-corrosive. At concentration of $[NA] > [NA]_{threshold, thermo}$, the crude will be corrosive.

In another embodiment for a crude, the threshold value of concentration of naphthenic acid is due to kinetic effects rather than thermodynamic effects. In this case, the threshold concentration of NA is greater than the equilibrium concentration, $[NA]_{threshold,\ thermo}$ (i.e., the concentration at which iron naphthenate is in equilibrium with NA). Instead, the value of the threshold concentration is that value at which iron oxidizes at a rate that exceeds a tolerable level. For illustration purposes, assume that the overall reaction presented in equation above consists of two steps and that the first step is the rate determining step:

$$Fe + R(CH_2)_n COOH \rightarrow (R(CH_2)_n COO)Fe + \tfrac{1}{2}H_2 \qquad (i)$$

$$(R(CH_2)_n COO)Fe + R(CH_2)_n COOH \rightarrow (R(CH_2)_n COO)_2 Fe + \tfrac{1}{2}H_2 \qquad (ii)$$

Since the first step is assumed to be the rate determining step, the rate of the corrosion of iron is determined to be:

$$I_{corr} = \text{rate constant} \times \text{reactants concentration} = k_{corr}[Fe][NA].$$

If the maximum tolerable rate of corrosion of iron is $I_{max}$, then the threshold value of naphthenic acid concentration is $[NA]_{threshold, kinetic} = \{I_{max}/k_{corr}[Fe]\}$. Since $[Fe]=1$, therefore $[NA]_{threshold, kinetic} = \{I_{max}/k_{corr}\}$.

Optimizing Crude Treatment Strategy

The method for characterizing the corrosion characteristics of crudes can also be used for defining and recommending optimal treatments for the crude or blends. In one embodiment, the data can be used to determine if a particular crude is compatible or not with a particular refinery and product requirements. In a second embodiment, the data can be used in a predictive engine or a model to predict the corrosiveness of particular crude samples or feedstock for a particular refinery. In another embodiment, the compiled information on a crude's corrosion characteristics can be used along with additional data, e.g., processing conditions, mass transfer characteristics, etc., to optimize the processing of the crudes.

Knowing the corrosion characteristics of the crude, the refinery can also determine the optimal dosage of chemical treatment and adjustment of performance parameters. Chemical treatment of the crude may also comprise additive treatment, for example, addition of desalting additives, corrosion passivation additives (typically used in distillation column), anti-foulants (used in various refinery processes). The adjustment of performance parameters may include for example, optimizing or adjusting process conditions according to the characteristics of the crude, e.g., temperature, contact time, total pressure or partial pressure of specific reactants in the process.

In yet another embodiment by being able to quantify the corrosion characteristics of different crudes and crude blends, the invention provides a way to assess the risk of using cheaper crudes. Treatment plans as well as corresponding cost as such is known prior to using the crudes, allow for the risk assessment as well as advanced planning to mitigate any performance degradation due to the use of particular crudes or crude blends.

System for Optimizing Crude Blend:

Embodiments of methods for characterizing the corrosivity of crudes can be implemented in processes and systems for continuous real-time analysis and control to effect optimizing the blending process. In one embodiment, such a system includes a plurality of supply lines for supplying different crudes.

The system further includes analyzing devices positioned in the supply lines for analyzing the crude composition for any of the characteristics as described. To blend the various supply streams to provide a final stream to a refinery, the system further includes a plurality of output lines, with the composition(s) and flow(s) of the blended streams being controlled and determined by signals provided by the analyzing devices resulting in the blending of the volumes of selected supply lines.

The blending can be done by an operator, e.g., a person, or the operator can be a person, an apparatus, an automatic system, or a combination thereof. The results of the on-line analyzer (e.g., a spectrometer, crystal microbalances output) are output to the system, with the system performing adjustments to the flow of the crudes according to or compared with identified characteristics (e.g., EIS signatures of the EI spectra, mass changes of the sample from crystal microbalances) or pre-determined parameter values (impedance measurements, etc.) of the crude feedstock to the refinery. Data correlating short-term corrosion rate measurements of the refinery feed with long-term corrosion performance of the referenced refinery feedstock (and/or laboratory-simulated crudes) can be used to specifically the blending for a feed with desired short-term corrosion measurements, which would correlate with an acceptable long-term corrosion performance. Blending of the supply lines may be facilitated by suitable mixing means including static mixer or on-line mixer. Flow control of the supply lines can be done via automatic flow control devices known in the art. In one embodiment, the composition(s) and/or flow(s) of the feedstock streams are automatically adjusted by comparing the measured values with pre-determined values, e.g., measured impedance, linear voltammogram, etc. of a reference crude oil having known corrosion properties. For example, for a plurality of crude from various sources, e.g., tank 1 (T1), tank 2 (T2), tank n (Tn) with each crude having a measured parameter value of $P_1$, $P_2$, and $P_n$. The measured parameters are compared to the parameter value $P_x$ of a referenced crude X, for an optimized crude blend. In one embodiment, the optimized crude blend comprises a mixture of blends from the various tanks and different rates according to: $\Sigma V_i P_i < P_x$, wherein V is a fraction based on any of concentration, mass volume, etc., P is the select control parameter, and $P_x$ is the acceptable or limit value of the select parameter. If the difference (between $\Sigma V_i P_i$ and $P_x$) is outside the acceptable range, e.g., greater than 1%, greater than 2%, greater than 5%, etc., the proportions of the crude feed streams are automatically adjusted via flow control devices (e.g., on-line in the refinery or connected to feed tanks), for the measured values to be comparable with the pre-determined values.

In one embodiment, the automatic system includes at least an on-line analyzer employing at least a crystal microbalance (QCM). The microbalances can be installed at pre-select locations. The pre-select locations in one embodiment are at inlets of all refinery feed streams. In another embodiment, the pre-select locations throughout the refinery, and particularly in equipment or processes that are susceptible to corrosive attacks. The working electrodes of the microbalance are exposed to the crude at its operating temperature. A constant heat flux is applied through the microbalance resulting in its working electrode having a variable temperature, or a variable heat flux is applied through the microbalance resulting in its working electrode having a constant temperature. The surface density and heat transfer resistance of samples (e.g., carbon steel or other structural materials) can be measured, corresponding ratio can be determined contributing to the mass changes of the samples due to the corrosivity of the crude feedstock.

In one embodiment, isothermal tests are conducted over a range of temperatures that typically span ambient to 750° F. to measure the mass changes of the samples over a short period of time, e.g., less than a day, are recorded. In another embodiment, the isothermal tests are conducted over a period of at least half an hour. The data can be used to correlate with a reference database containing collected data from known corrosion performance of reference refinery feedstock samples, which reference data was previously collected for similar samples.

In one embodiment, the automatic system includes means for automatic feeding of additives including but not limited to corrosion inhibitors in response to the identified characteristics, for a controlled/optimized crude blend having desired characteristics, e.g., impedance values, spectroscopy measurements, etc., corresponding to a blend with optimized dissociation of acids, molecular associations, or dissociation of ionic sulfur species with the desired corrosion characteristics.

EXAMPLES

The following illustrative examples are intended to be non-limiting.

Example 1

In this example, the dissociation of two single acids, decanoic acid (DA) and cyclohexanepropionic acid (CHPA), is shown to be a factor in the corrosivity of a crude. The electrical resistivity of solutions consisting of DA dissolved in mineral oil and CHPA dissolved in mineral oil are measured as a function of temperature, and the results show that the acid molecules dissociate into $H^+ + R(CH)_{2n}COO^-$ in hydrocarbons.

In this example, the concentration of the acids is kept in the range from 1% to 4%. The solution's electrical resistivity is obtained from the AC impedance at high frequencies (e.g., 10 kHz) of a cell composed of two Pt electrodes immersed in approximately 0.25 liter of solution. Measurements are conducted at increments of 50° F. from 200° F. to 529° F., the boiling point of CHPA, or 516° F., the boiling point of DA. As the dissociation of the acid occurs, there is a sudden decrease in high frequency impedance as the temperature is increased.

Example 2

This example demonstrates the ability of the proposed techniques to reveal that mixtures of carboxylic acids and NA facilitate dissociation of the acids. Example 1 is duplicated with solutions of other single types of carboxylic acid and of NA, and solutions containing a mixture of several types of carboxylic acids and several types of NA. Four acids are tested. The first two are at the light and heavy end of the family that includes CHPA: cyclopentane carboxylic acid (CPCA, $T_{BP}$=216° C.) and cyclohexane butyric acid (CHBA). The second set of acids is from the light and heavy ends of the group that includes DA: butanoic acid (BA) and hexadecanoic acid (HDA).

The measurements of solution's resistivity are conducted as a function of temperature, showing the dissociation of the acid (sudden decrease in high frequency impedance (and/or decrease in DC resistivity measured by 2 pt probe or 4 pt probe in high purity quartz cell) as the temperature increases).

Example 3

In this example, the effect of solvents on the acid dissociation is demonstrated as a way to evaluate corrosivity in different hydrocarbons. Six acid types employed in the previous examples are mixed with three different types of solvents for a total of 18 solutions, each consisting of one acid and one solvent. The first solvent, cyclodecane, is from the group of cycloalkanes. Pyrene is an aromatic, and 1-methylindane is a cycloalkanoaromatic. In addition to the above solvent, mineral oil is also used as the fourth solvent. For each solvent, two solutions are prepared with equal concentrations of all three acids from the same family and one solution is mixed with equal concentrations of the six acids, for a total of nine solutions.

The equipment set up is similar to the set up in Example 1. The solution resistance is measured as a function of temperature up to a temperature that is a few degrees lower than the boiling point of the solution's most volatile component.

Example 4

In this example, acid dissociation in a crude is measured as a function of temperature, illustrating a way to evaluate corrosivity in a refinery feedstock. Electrical resistivity obtained from EIS at high frequencies and the two-point or four point probe measurement in a high purity quartz cell is used to correlate the acid dissociation with the boiling point of the crude.

Example 5

This example illustrates a method to quantify corrosion by measuring the break-up of NA-dimers as function of temperature (corrosivity). The same solutions in the previous examples to investigate the dissociation of individual acid molecules are employed in Example 5 to investigate the association of two or more acid molecules. Specifically, six acids (BA, DA, and HDA; along with CPCA, CHPA, and CHBA) and four solvents (mineral oil, cyclodecane, pyrene, and 1-methylindane) will be mixed to form 24 solutions, each composed of a single acid and a single solvent.

Structural analyses of the solutions are conducted as a function of temperature, starting at 200° F. and raising the temperature in increments of 50° F., but not exceeding the boiling point of the solution's most volatile component. Raman spectroscopy is used to determine the disassociation of the acid molecules in the bulk of the solution into dimers, trimers, etc., showing the temperature dependency of corrosion to govern the temperature-dependent structural change in the solution (e.g., the break-up of dimers, trimers, etc.).

Example 6

In this example, the role of solvents and acids in the break-up of NA-dimers are demonstrated. The experiment is conducted to determine if dissimilar acids are more or less likely to form molecular associations and if the type of solvent influences the formation of asymmetric molecular associations. Example 5 is duplicated on solutions with equal concentrations of the three linear acids (BA, DA, HDA), equal concentrations of the three cyclic acids (CPCA, CHPA, CHBA), and equal concentrations of the six acids: BA, DA, HAD, CPCA, CHPA and CHBA. Each of the three combinations of acids is mixed with the four solvents: mineral oil, cyclodecane, pyrene, and 1-methylindane for a total of 12 solutions.

Example 7

It is theorized that metal surfaces (bare or oxide covered) catalyze the breakup of NAs. If so, the individual molecules are present on the metal's surface and available for reaction with the metal even though the NAs are tied up as dimers, trimers, tetramers, micelles, etc., in the bulk of the solution. In this example, surface enhanced Raman spectroscopy (SERS) is used to investigate in situ the possible break-up of molecular associations of Example 6 solutions on the surfaces of metals such as carbon steel, 13Cr-ferritic stainless steel, 304 austenitic stainless steel and 316 stainless steel. SERS is selected because it can identify sub-monolayer quantities of the species present on the metal's surface as the metal is immersed in the solution.

The solutions (from Example 6) are contained in heated glass cells (400°-700° F.), with each glass cell containing a solution and a steel sample. The maximum temperature for each solution is maintained at a few degrees below the boiling point of the solution's most volatile component. The solution is saturated with ultra-high purity nitrogen to remove air, especially oxygen, from the solution. Each steel sample contains gold nanoparticles that were electrodeposited onto the steel's surface from aqueous 5 mM $AuCl_3$. The gold nanoparticles are required to enhance the optical field of the laser at the steel's surface. SERS is measured for gold samples to confirm that gold does not cause the breakup of associated groups of NA molecules. Results are collected correlating acid dissociation with the boiling point of the solutions.

Example 8

Each test solution will consist of a single sulfur compound listed in Table I and one hydrocarbon solvent listed in Table II. The combination of four hydrocarbon solvents and 14 sulfur compounds will yield 56 solutions of a single solvent+single sulfur compound.

TABLE 1

| Sulfur compounds | | Boiling Point |
|---|---|---|
| Mercaptans | | |
| Benzylmercaptan | $PhCH_2SH$ | 194° C. (381° F.) |
| 1-octanethiol | $CH_3(CH_2)_7SH$ | 199° C. (390° F.) |
| 1,5-Pentanedithiol | $HS(CH_2)_5SH$ | 217° C. (423° F.) |
| 1-dodecanethiol | $(CH_3(CH_2)_{11}SH$ | 270° C. (518° F.) |
| Sulfides | | |
| Dimethyl disulfide | $CH_3SSCH_3$ | 110° C. (230° F.) |
| Diallylsulfide | $(CH_2\!\!=\!\!CHCH_2)_2S$ | 139° C. (282° F.) |
| Dipropylsulfide | $(CH_3CH_2CH_2)_2S$ | 141° C. (286° F.) |
| Dibutyldisulfide | $(CH_3CH_2CH_2CH_2)_2S_2$ | 230° C. (446° F.) |
| Diphenylsulfide | Ph—S—Ph | 296° C. (565° F.) |
| Thiophenes | | |
| 2-methylthiophene | | 113° C. (235° F.) |
| tetrahydrothiophene | | 119° C. (246° F.) |
| 2,5-dimethylthiophene | | 136° C. (277° F.) |
| Benzothiophenes | | |
| 1-Benzothiophene | | 221° C. (430° F.) |

TABLE 1-continued

| Sulfur compounds | Boiling Point |
|---|---|
| Dibenzothiophenes | |
| Dibenzothiophene | 332° C. (630° F.) |
| Benzonaphtothiophene | |

*** Ph-phenyl ring = $C_6H_5$—; Benzyl group = $C_6H_5CH_2$—; Thiophene = cyclic: $C_4H_4S$

TABLE II

| Solvents | BP |
|---|---|
| Mineral Oil | 260° C.-393° C. |
| (Alkanes | (500°-740° F.) |
| Decane | 174° C. (345° F.) |
| Dodecane | 216° C. (421° F.) |
| Cycloalkanes | |
| Cyclopentane | |
| Cyclodecane | ≈179° C. (355° F.) |
| Bicyclohexyl | |
| Aromatics | |
| Pyrene | 404° C. (759° F.) |
| Cycloalkanoaromatics | |
| 1-methylindane | 177° C. (350° F.) |

The dissociation of sulfur compounds can be measured using the same experimental technique employed to investigate the dissociation of NAs, e.g., with electrochemical impedance spectroscopy (EIS), and two-point probe and four-point probe measurements of DC resistivity conducted in a high purity quartz cell as a function of temperature (200° F.-650° F.) on solutions composed of various hydrocarbon solvents found in crude and one type of sulfur-containing molecule. Voltammetry of UMEs can also be used to fingerprint the various sulfur species present in the crude oil and correlated corrosion impact.

Tests of the dissociation of sulfur compounds can also be conducted on solutions composed of hydrocarbon solvents plus one sulfur compound and one type of naphthenic acid molecule. Here the objective is to determine if there is a synergistic effect in the dissociation of either the sulfur compound or the naphthenic acid.

Example 9

In this example, more solutions are prepared by adding either DA (Decanoic Acid) or CHPA (cyclohexanepropionic acid) to each of the 56 solutions composed of a hydrocarbon and a sulfur compound. DA and CHPA were selected because of their relatively high corrosivity toward carbon steel. EIS can also be conducted on the solutions as a function of temperature at 50° F. intervals from 200° F. to the maximum temperature listed for each solution (respective boiling points). The results of the test are expected to reveal a synergistic effect between the NAs and sulfur compounds, which causes ionization of the solutions and hence with direct consequence on the corrosivity Example 10

Crude oil sample of refinery feed stock is prepared and organic acids are extracted from the crude sample by methods known in the art to extract the acids. The samples are compared with "controlled" crudes with known corrosion rates as measured in the lab or in a refinery setting. After the extraction of the acids, all the crudes are analyzed/characterized by computation of acid stability (both acid dimerization energies and acid dissociation energies). Dimerization energies are calculated using quantum chemical optimization. The corrosivity of the new sample is predicted by comparing the dimerization and dissociation energies as a function of temperature. Once the corrosion rates of the new samples are verified, a database of corrosivity and computation of a number of crudes is established and built-up over time.

Other Examples

In addition to the use of EIS as demonstrated in the examples above, examples 1-9 are duplicated with the use of linear/cyclic voltammetry. In another set of examples, DC two-point and four-point probes are employed in a high purity quartz cell. In these additional examples, corrosion tests of carbon steels coupons are carried out in the same solutions to record the measurable changes in the test parameters in the process of establishing a database of corrosivity and acid stability.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention, inclusive of the stated value and has the meaning including the degree of error associated with measurement of the particular quantity.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the use of "may" or "may be" indicates that a modified term is appropriate, capable, or suitable for an indicated capacity, function, or usage, while taking into account that in some circumstances the modified term may sometimes not be appropriate, capable, or suitable.

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated by reference.

What is claimed is:
1. A method for evaluating the corrosivity of a crude oil, comprising:
  withdrawing a representative sample of a crude oil feedstock to a refinery;
  performing impedance measurements on the crude oil sample as a function of temperature to obtain a first electrochemical impedance spectroscopy (EIS) data, wherein the first EIS data include data at 10 kHz frequency;

deriving at least one of a resistance reading and a dielectric constant reading for the first EIS data;

obtaining a second EIS data on a reference crude oil sample having known corrosion properties, wherein the second EIS data include data at the 10 kHz frequency;

deriving at least one of a resistance reading and a dielectric constant reading for the second EIS data;

analyzing the first EIS data relative to the second EIS data to evaluate the corrosivity of the crude oil feedstock, wherein the step of comparing the first EIS data with the second EIS data including comparing at least one of a resistance reading and a dielectric constant reading of the first EIS data with the second EIS data.

2. The method of claim 1, wherein the impedance measurements are carried out using a two-electrode chemical cell with an ultramicroelectrode as working electrode and a second electrode serving as both reference electrode and counter electrode.

3. The method of claim 1, wherein the ultramicroelectrode comprises platinum.

4. The method of claim 1, wherein the impedance measurements are carried out at a temperature ranging from ambient to 700° F.

5. The method of claim 1, wherein the impedance measurements are carried out as a function of temperature and oxygen concentration, wherein the crude oil is enriched with oxygen at a concentration from 10 to 500 ppm $O_2$.

6. The method of claim 1, wherein the impedance measurements are carried out as a function of temperature and oxygen concentration, and wherein the crude oil is enriched with water and/or steam at a concentration from 2 ppm to 2 wt. %.

7. The method of claim 1, wherein the step of analyzing the first EIS data relative to the second EIS data comprises using statistical techniques.

8. The method of claim 7, wherein the statistical techniques include at least one of Principal Component Analysis, Multivariate Least Squares Regression, Principal Component Regression, Pattern Recognition analysis, Cluster analysis, Neural Net analysis, and Group Methods of Data Handling.

9. The method of claim 1, wherein the step of analyzing the first EIS data relative to the second EIS data comprises using a look up table containing EIS data correlating to corrosion properties of a plurality of reference crude oil samples.

10. The method of claim 1, wherein obtaining a second EIS data on a reference crude oil sample having known corrosion properties comprises adding known concentrations of acids to the reference crude oil sample to measure dissociation of the acids in the reference crude oil sample.

11. The method of claim 10, wherein obtaining a second EIS data on a reference crude oil sample having known corrosion properties further comprises obtaining impedance measurements as a function of temperature on the reference crude oil sample having known concentrations of acids.

12. The method of claim 11, wherein the impedance measurements of the reference crude oil sample are carried out at a temperature ranging from ambient to 700° F.

13. The method of claim 1, wherein obtaining a second EIS data on a reference crude oil having known corrosion properties comprises adding known concentrations of sulfur compounds to the reference crude oil sample to measure dissociation of the sulfur into ionic species in the reference crude oil sample.

14. A method for evaluating the corrosivity of a crude oil feedstock by correlating its corrosivity with dissociation of acids in the crude oil, comprising:

withdrawing a representative sample of the crude oil feedstock, wherein the crude oil feedstock has a certain amount of acids;

detecting the dissociation of the acids in the crude oil feedstock sample as a function of temperature by obtaining impedance measurements of the crude oil feedstock over a range of temperature from ambient to 700° F.;

providing impedance measurements of at least a reference oil feedstock having a known dissociation of acids;

comparing the impedance measurements of the crude oil feedstock sample with the impedance measurements of the reference oil feedstock to evaluate the corrosivity of the crude oil feedstock;

wherein the impedance measurements of the crude oil feedstock sample and the reference oil feedstock are carried out using a two-electrode chemical cell with an ultramicroelectrode as working electrode and a second electrode serving as both reference electrode and counter electrode.

15. The method of claim 14, further comprising using a look up table to evaluate the corrosivity of the crude oil feedstock sample.

16. The method of claim 14, wherein the impedance measurements of the reference oil feedstock having a known dissociation of acids are measured before and after adding a known concentration of acids to the reference oil feedstock.

17. The method of claim 14, wherein the impedance measurements of the crude oil feedstock sample are carried out as a function of temperature and oxygen concentration and wherein the crude oil feedstock sample is enriched with oxygen at a concentration from 10 to 10,000 ppm $O_2$.

18. A method for evaluating the corrosivity of a crude oil feedstock in operations by correlating its corrosivity with molecular associations of naphthenic acid in the crude oil feedstock upon contact with at least a metal, comprising:

withdrawing a representative sample of the crude oil feedstock, wherein the crude oil feedstock has a certain amount of naphthenic acid;

exposing a metal specimen to the crude oil feedstock sample;

detecting the molecular associations of naphthenic acid in the crude oil feedstock sample upon exposure to the metal specimen as a function of temperature by obtaining electrical resistivity measurements of the crude oil feedstock sample over a range of temperature from ambient to 700° F.;

providing resistivity measurements of at least a reference oil feedstock having a known corrosion rate upon exposure to the metal specimen;

comparing the resistivity measurements of the crude oil feedstock sample with the resistivity measurements of the reference oil feedstock to evaluate the corrosivity of the crude oil feedstock.

19. The method of claim 18, wherein the electrical resistivity measurements are obtained via a four-point probe instrument.

20. The method of claim 18, wherein the electrical resistivity measurements are obtained via a four-point probe instrument comprising platinum electrodes.

* * * * *